(12) United States Patent
Hladiy et al.

(10) Patent No.: US 6,713,649 B1
(45) Date of Patent: Mar. 30, 2004

(54) METHOD FOR PRODUCTION OF FORMIC ACID

(75) Inventors: Serhiy Hladiy, Boryslav (UA); Mykhaylo Starchevskyy, Boryslav (UA); Yuriy Pazderskyy, Boryslav (UA); Yaroslav Lastovyak, Drohobych (UA)

(73) Assignee: BASF Aktiengesellschaft, Ludwigshafen (DE)

( * ) Notice: Subject to any disclaimer, the term of this patent is extended or adjusted under 35 U.S.C. 154(b) by 46 days.

(21) Appl. No.: 10/129,511

(22) PCT Filed: Nov. 8, 2000

(86) PCT No.: PCT/EP01/11046

§ 371 (c)(1),
(2), (4) Date: May 6, 2002

(87) PCT Pub. No.: WO01/34545

PCT Pub. Date: May 17, 2001

(30) Foreign Application Priority Data

Nov. 9, 1999 (DE) .......................................... 199 53 832

(51) Int. Cl.⁷ .......................... C07C 53/02; C07B 53/00
(52) U.S. Cl. ........................................ 562/609; 562/606
(58) Field of Search ................................ 562/606, 609; 203/84

(56) References Cited

U.S. PATENT DOCUMENTS 2,160,064 A  5/1939  Eversole
4,326,073 A  4/1982  Wolf et al.
4,584,390 A * 4/1986 Dieckelmann et al. ...... 549/526

FOREIGN PATENT DOCUMENTS

EP  017 866  10/1980

* cited by examiner

Primary Examiner—Shailendra Kumar
Assistant Examiner—Karl Puttlitz
(74) Attorney, Agent, or Firm—Keil & Weinkauf

(57) ABSTRACT

The invention relates to a process for the preparation of formic acid, comprising the following steps:
  a) hydrolysis of methyl formate to give a mixture of water, formic acid, methanol and excess methyl formate;
  b) removal of the methanol and excess methyl formate from the mixture of water, formic acid, methanol and excess methyl formate by distillation to give aqueous formic acid;
  c) extraction of the aqueous formic acid with at least one formic acid ester to give a mixture of said at least one formic acid ester and formic acid;
  d) separation of said at least one formic acid ester and formic acid by distillation.

The process according to the invention enables gentle preparation of formic acid. Only very slight decomposition of formic acid occurs, and the formic acid exhibits only a slight corrosion action under the reaction conditions according to the invention.

8 Claims, 1 Drawing Sheet

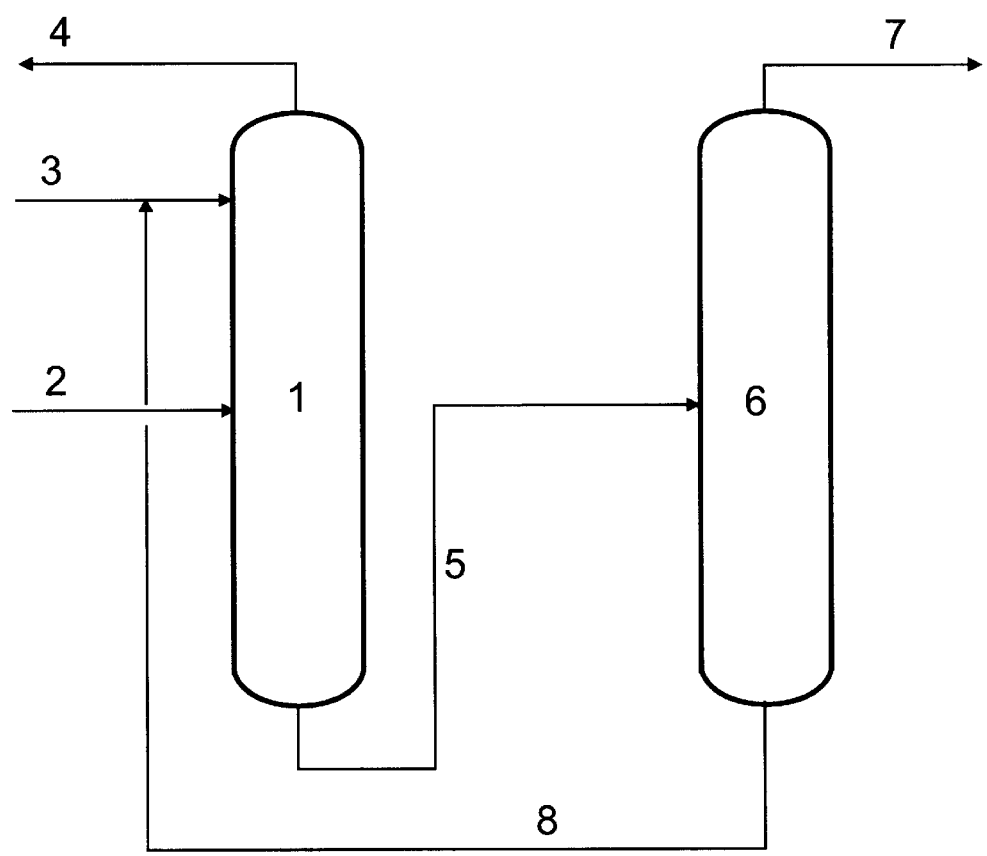

METHOD FOR PRODUCTION OF FORMIC ACID

BACKGROUND

The present invention relates to a process for the preparation of formic acid.

More recent processes for the preparation of formic acid on an industrial scale start from methyl formate, which is easily accessible by carbonylation of methanol. The methyl formate is subsequently hydrolyzed, with the formic acid acting as catalyst. Since both the hydrolysis and the re-esterification are catalyzed, an equilibrium becomes established in which all four components, methyl formate, water, formic acid and methanol, are present in high proportions.

This results in problems in performing the reaction. It is not possible to shift the equilibrium by removing the desired process products by distillation since the methyl formate (boiling point 32° C.) has a significantly lower boiling point than methanol (boiling point 65° C.) and formic acid (boiling point 101° C.). It would therefore be favorable to shift the equilibrium to the formic acid side by means of an excess of water.

Further problems occur in working up the aqueous formic acid. Formic acid and water form an azeotrope which contains 77.5% by weight of HCOOH and boils at 107.1° C. at 101.3 kPa. The aqueous formic acid formed on hydrolysis of methyl formate has an acid content of from about 20 to 60% by weight. Pure or more highly concentrated formic acid therefore cannot easily be recovered from these dilute aqueous formic acid solutions by distillation.

U.S. Pat. No. 2,160,064 proposes separating the azeotrope by distillation at various pressures. To this end, the dilute acid is first separated at relatively high pressure into water as the top product and a formic acid-rich azeotrope as the bottom product. This azeotrope is subsequently distilled again in a second column operated at relatively low pressure. This gives formic acid as the top product and an azeotrope having a lower acid content than that from the first distillation step as the bottom product. The azeotrope from the second step is fed back into the first step.

In a practical implementation, the distillation is carried out at a pressure of from approximately 202.6 to 303.9 kPa. This causes the composition of the azeotrope to shift toward a higher acid content. Theoretically, the azeotrope should contain from approximately 84 to 85% by weight of formic acid at 253.2 kPa. When the distillation is carried out in practice, the formic acid content in the still of the first distillation column never exceeds a proportion of from 81 to 82% by weight. The second distillation is carried out at atmospheric pressure or somewhat below atmospheric pressure. This means that the amount of formic acid distilled off can correspond to the difference between the compositions of the two azeotropes. Owing to the small differences, the columns must have a very high number of theoretical plates and be operated at very high reflux ratios. At a reflux ratio of R=2.3, the number of theoretical plates for the first distillation column is 15. The second column has, at a reflux ratio of R=10, 18 theoretical plates. Furthermore, the azeotrope formed as the bottom product in the second distillation must be fed back to the first distillation step.

Both owing to the high bottom temperature (125 to 135° C.) in the first column and owing to the high residence time of the formic acid, high losses of yield due to decomposition of the formic acid must be accepted. Furthermore, the aggressive nature of aqueous formic acid means that distillation columns made from special materials must be used in order to avoid excessive corrosion. Owing to the large product streams in circulation and the high energy consumption, the process described is therefore unsuitable for use on an industrial scale.

A switch has therefore been made to removing the formic acid from its mixture (with water) by extraction with water, with the extractant and the formic acid being separated by distillation in a further step. A process of this type is proposed, for example in EP 0 017 866 B1, where firstly methyl formate is hydrolyzed, and the methanol and excess methyl formate are removed from the resultant hydrolysis mixture by distillation. The bottom product from the distillation, consisting of formic acid and water, is extracted in a liquid extraction with an extractant which principally takes up the formic acid. The preferred extractants proposed are carboxamides, in particular N-di-n-butylformamide, N-di-n-butylacetamide, N-methyl-N-2-heptylformamide, N-n-butyl-N-2-ethylhexylformamide, N-n-butyl-N-cyclohexylformamide, N-ethylformanilide and mixtures of these compounds. Further suitable extractants described include isopropyl ether, methyl isobutyl ketone, ethyl acetate, tributyl phosphate and butanediol formate. The mixture obtained in the extraction, comprising formic acid, the extractant and some of the water, is subjected to a further distillation. A product consisting of all or some of the water introduced into the distillation and some of the formic acid is taken off at the top of the column and fed back in vapor form into the lower part of the first distillation column. The bottom product is a mixture of extractant, possibly some of the water and the majority of the formic acid. This mixture is separated into anhydrous or substantially anhydrous formic acid and the extractant in a further, third distillation column. The extractant is recycled into the process. In a particular embodiment, the first and second distillation steps are combined in a single column. However, the extraction of the formic acid from the aqueous mixture is still carried out in a separate extractor. To this end, the mixture of formic acid and water is removed from the column via a side outlet and fed to the extractor. The mixture of extractant and formic acid and possibly water is discharged from the extractor and fed back below the side outlet of the distillation column. A mixture of formic acid, extractant and possibly water is removed at the bottom of the column and fed to a further distillation column, which corresponds to the third distillation column in the embodiment described above.

The design of large-scale industrial syntheses is determined to a large extent by economic considerations. It is therefore an object of the present invention to provide a process for the preparation of formic acid which employs inexpensive chemicals which are available on a large industrial scale and should not be harmful to the environment, and which can be carried out in smaller plants compared with the processes known from the prior art with the same yield.

BRIEF SUMMARY OF THE INVENTION

We have found that this object is achieved by a process for the preparation of formic acid which comprises the following steps:
a) hydrolysis of methyl formate to give a mixture of water, formic acid, methanol and excess methyl formate;
b) removal of the methanol and excess methyl formate from the mixture of water, formic acid, methanol and excess methyl formate by distillation to give aqueous formic acid;

c) extraction of the aqueous formic acid with at least one formic acid ester to give a mixture of at least one formic acid ester and formic acid;

d) separation of at least one formic acid ester and formic acid by distillation.

DETAILED DESCRIPTION OF THE INVENTION

In a practical implementation on a technical scale it is preferred to use at least one formic ester of the group consisting of ethylene glycol diformate, diethylene glycol diformate, propane-1,2-diol diformate, propane-2,3-diol diformate, Dipropylene glycol diformate, butane-2,3-diol diformate, butane-1,4-diol diformate, benzyl formate, cyclohexyl formate, 2-phenylformate, 2-ethylhexylformate. Those formic acid esters are produced in large scale and are therefore available in huge amounts at low costs. Benzyl formate is most preferred.

Benzyl formate is a colorless liquid with a slight cinnamon odor. It has a density of 1.04 g/cm3 and a boiling point of 202.3° C. With water, benzyl formate forms an azeotrope having a water content of 80% by weight and a boiling point of 99.2° C. Benzyl formate has ideal properties as an extractant. The boiling point is sufficiently high to allow effective and simple separation of the formic acid by distillation. At the same time, no significant decomposition of the formic acid is observed at the requisite temperatures. The formic acid is therefore only subjected to very low thermal stresses in the process according to the invention and consequently only slight decomposition of the formic acid need be accepted. Furthermore, the formic acid is in comparatively low concentration both in the aqueous solution and in the extractant. Together with the low temperatures necessary in the process according to the invention, this results in an only low corrosion action of the formic acid. Apart from the distillative separation of formic acid and extractant provided as the final step, less resistant and thus less expensive materials can therefore be used for construction of the plant. Benzyl formate is a compound which is stable under the reaction conditions in the process. There is therefore no need to remove extractant decomposition products during work-up. Furthermore, benzyl formate does not interact with the compounds used in the process. A further advantage is the lack of toxicity of benzyl formate. Such esters can occur naturally in relatively large amounts as aroma substances in various fruit. They are also used in perfumes and as aroma substances in foods. Finally, benzyl formate is prepared from benzyl alcohol, which, as a bulk chemical, is available in virtually unlimited amounts at low prices. The advantages presented for benzyl formate of course also apply to all other formic acid esters mentioned above to a more or less extent.

The extraction is advantageously carried out under distillation conditions in an extractive distillation column. There is therefore no need for a separate extractor. A mixture comprising the majority of the water, a little formic acid and small amounts of the extractant benzyl formate is taken off at the top of the column. This mixture is fed back to the hydrolysis reactor, in which hydrolysis of the methyl formate takes place. A mixture consisting of small amounts of water, the majority of the formic acid and the majority of the extractant is taken off at the bottom of the column.

The formic acid ester need not be introduced as such. It is also advantageously possible to employ the corresponding alcohol. These react with the formic acid "in situ" under the conditions of the extractive distillation to give formic acid esters. The reaction equilibrium between the formic acid ester and the alcohol means that small amounts of alcohol are always present in the reaction mixture during the process. However especially in case of benzyl alcohol, these do not interfere further since benzyl alcohol has comparable physical properties to benzyl formate. Benzyl alcohol has a density of 1.04 g/cm3 and a boiling point of 205.3° C. With water, it forms an azeotrope containing 91% by weight of H2O and boiling at 99.9° C. In the practical implementation of the process, the mixture of benzyl formate and benzyl alcohol can therefore be regarded as a single substance owing to the comparable physical properties and the rapid reaction between the two substances.

The benzyl formate is advantageously introduced at the top of the extractive distillation column.

The extractive distillation column is advantageously operated at ambient pressure.

In an advantageous embodiment, a phase separator is provided at the top of the extractive distillation column. The mixture of water, a little formic acid and a little extractant taken off at the top of the column can then be fed to the separator, where the aqueous phase and the extractant phase can be separated and the extractant then fed back to the extractive distillation column.

The mixture of formic acid, benzyl formate and possibly small amounts of water which is taken off at the bottom of the extractive distillation column is worked up by distillation. It has proven advantageous here to carry out the separation of the mixture of benzyl formate and formic acid at reduced pressure in a vacuum column. This reduces the thermal stress on the formic acid, further reducing losses due to decomposition. Furthermore, the lower distillation temperature has an advantageous effect on the energy balance and thus on the costs of the process.

The formic acid ester can be circulated between the extractive distillation column and the vacuum column, which means that only small unavoidable losses of extractant need to be made up.

The water content in the bottom product mixture in the extractive distillation column is determined by the formic acid ester content e.g. the benzyl formate content. The process according to the invention therefore allows the preparation of both anhydrous formic acid and aqueous formic acid having a certain water content. The amount of formic acid ester is therefore advantageously selected depending on the water content of the formic acid to be prepared.

The extractive distillation column is advantageously operated at a low reflux ratio.

BRIEF DESCRIPTION OF THE DRAWING

The invention is illustrated in greater detail below with reference to examples and with reference to a drawing, in which:

FIG. 1 shows a schematic representation of an apparatus for carrying out the process according to the invention.

In FIG. 1, 1 denotes an extractive distillation column, to which a mixture of formic acid and water is fed via line 2 from the hydrolysis reactor (not shown) after removal of methanol and excess methyl formate. If the reaction is carried out appropriately, the mixture may also contain small amounts of the extractant benzyl formate. The feed of the hydrolysis mixture takes place approximately in the center of the extractive distillation column. The feed of the extractant benzyl formate takes place via line 3 close to the top of the column. During continuous operation of the plant, only the unavoidable losses of extractant need to be compensated for. The majority of the extractant is circulated. A mixture comprising the majority of the water and small amounts of formic acid and extractant is taken off at the top of the extractive distillation column via outlet line 4. The extractant can, if desired, be removed in a phase separator (not shown). The mixture is fed back into the hydrolysis reactor (not shown). A mixture comprising the majority of the formic acid and of the extractant and possibly small amounts of water is discharged at the bottom of the extractive distillation column 1 via line 5. Line 5 runs into a vacuum column 6, the feed taking place approximately in the center of the height of the column. Formic acid, possibly containing small amounts of water, is taken off at the top of the column via outlet line 7. The extractant, which is virtually free from formic acid and water, is taken off at the bottom of the column and fed back to the extractive distillation column 1 via circulation line 8 and feed line 3.

Under the conditions indicated, decomposition of the extractant was not observed.

The conditions for carrying out the extractive distillation and the separation of the mixture of benzyl formate and formic acid are explained more precisely with reference to the following examples.

1. Distillation

1.1 Distillation column

A glass column having an internal diameter of 20 mm was packed with glass rings (4 mm) to a height of 1.470 m. The height of a theoretical plate was determined as 84 mm using a benzene/dichloromethane standard mixture. The feed stream was introduced at the height of the 11th theoretical plate. The extractant was introduced at the top of the column. A phase separator, in which the distilled-off mixture was separated into extractant and aqueous formic acid, was installed at the top of the column. The capacity of the column still was 500 cm3.

1.2 Process Conditions for the Distillation

The column was operated at atmospheric pressure. Compositions having various water and formic acid contents were introduced and, after the process parameters had been established, the composition of the distillate taken off at the top of the column and the extract taken off at the bottom was investigated. The process conditions in the column were as follows.

| Location | Feed line | Top | Bottom |
|---|---|---|---|
| Temperature, ° C. | 101 to 105 | 98 to 99 | 115 to 145 |

The distillate taken off at the top of the column contained, at 99° C., 98.8% by weight of H2O, 0.6% by weight of the formic acid and 0.6% by weight of benzyl formate.

The results obtained for various molar ratios of benzyl formate and formic acid are shown in table 1.

TABLE 1

Extractive distillation at a high molar ratio of benzyl formate and formic acid

| Proportion of HCOOH in the feed, % by wt. | Feed (F), g/h | Molar ratio E/F | HCOOH content in the outlet stream, % by wt. | | |
|---|---|---|---|---|---|
| | | | Distillate | Extract | Relative to H$_2$O |
| 35.0 | 50 | 3.00 | 0.3 | 12.2 | 92.4 |
| 50.0 | 50 | 2.50 | 0.4 | 11.7 | 94.3 |
| 50.0 | 50 | 3.40 | 0.3 | 8.8 | 95.3 |
| 70.0 | 50 | 1.31 | 0.5 | 23.0 | 89.9 |
| 70.0 | 37.5 | 1.74 | 0.5 | 20.7 | 90.4 |
| 70.0 | 37.5 | 2.32 | 0.4 | 17.6 | 91.8 |

E: Benzyl formate
F: Formic acid

1.3 Vacuum Distillation of the Mixture of Formic Acid and Benzyl Formate

The distillation was carried out using the same column as described under 1.1. The distillation was carried out at a pressure of from 13.3 to 14.7 kPa. The temperatures in the column were as follows:

| Location | Feed line | Top | Bottom |
|---|---|---|---|
| Temperature, ° C. | 101 to 105 | 50 to 52 | 143 to 145 |

The data obtained in the distillation are shown in Table 2.

TABLE 2

Distillation of formic acid from an extract

| | Content, % by weight | | |
|---|---|---|---|
| Stream | HCOOH | H2O | Benzyl formate |
| Feed stream | 9.0 | 0.4 | 90.6 |
| Distillate | 94.3 | 5.7 | ~0.01 |
| Bottom | 0.3 | ~0.01 | 99.7 |

In each case, a defined mixture of water, formic acid and benzyl formate was introduced into a 500 ml flask fitted with reflux condenser and distillation bridge and was heated to the boil. When the equilibrium had become established, 1 ml of the distillate was removed in each case and its composition analyzed. The composition of the mixture in the flask was in each case varied in such a way that the starting proportion of benzyl formate was constant in each case and the water/formic acid ratio was varied.

In a first series of experiments, the proportion of benzyl formate was selected as 30 mol-%. Table 3 shows in each case the water content in the liquid phase (X) and in the vapor phase (Y) relative to formic acid.

TABLE 3

Content of H2O (mol-%) in the liquid and vapor phases (30 mol-% of benzyl formate)

| X | 9.31 | 18.41 | 24.52 | 33.20 | 41.59 | 50.05 | 61.71 | 69.90 | 83.75 | 92.50 |
|---|------|-------|-------|-------|-------|-------|-------|-------|-------|-------|
| Y | 4.53 | 19.52 | 32.27 | 42.93 | 58.46 | 63.03 | 73.85 | 82.45 | 92.55 | 97.12 |

At a proportion of benzyl formate of 30 mol-%, the composition of the H2O/formic acid azeotrope is 17.5 mol-% of H2O.

In a second series of experiments, the proportion of benzyl formate was set at 45.0 mol-%. The proportion of water in the liquid and vapor phases is shown in Table 4.

TABLE 4

Content of H2O (mol-%) in the liquid and vapor phases (45 mol-% of benzyl formate)

| X | 2.11  | 5.16  | 7.36  | 12.87 | 16.99 | 25.35 | 27.12 |
|---|-------|-------|-------|-------|-------|-------|-------|
| Y | 2.66  | 6.73  | 10.62 | 16.30 | 22.97 | 39.90 | 36.56 |
| X | 31.82 | 40.18 | 46.63 | 51.30 | 70.80 | 88.44 | 94.50 |
| Y | 45.56 | 58.42 | 64.71 | 68.12 | 85.22 | 96.35 | 38.08 |

At a proportion of 45 mol-% of benzyl formate, the mixture of H2O and formic acid no longer forms an azeotrope. The equilibrium data can be used to determine the minimum reflux ratio necessary and the number of theoretical plates for the extractive distillation column. In this case, the minimum reflux ratio necessary is Rmin=0.6. The number of theoretical plates is 9 for the lower part and 4 for the upper part of the extractive distillation column.

3. Equilibrium Distribution in the Water/Formic Acid/Benzyl Formate System in the Liquid Phase A mixture of water (10.0061 g) and benzyl formate (E, 10.7949 g) was in each case introduced into a thermostated glass vessel and stirred at 20.0 (±0.2)° C. In each case, a small amount of formic acid was added to this mixture. After vigorous mixing, the stirrer was stopped and phase separation was awaited. Samples were in each case taken from the water phase and the benzyl formate phase and their formic acid content analyzed. The values determined are given in Table 5.

TABLE 5

Distribution of formic acid between water and benzyl formate at 20° C.

| HCCOH | Benzyl formate, % by wt. | | | | Water, % by wt. | | | |
|-------|---|---|---|---|---|---|---|---|
| g | E | HCOOH | H2O | BA | H2O | HCOOH | E | BA |
| 0 | 92.9 | 0 | 1.5 | 5.6 | 99.1 | 0 | 0.5 | 0.4 |
| 0.5861 | 88.4 | 0.8 | 2.1 | 8.7 | 89.0 | 9.8 | 0.7 | 0.5 |
| 1.5912 | 86.9 | 2.1 | 2.3 | 8.7 | 82.9 | 15.2 | 1.2 | 0.7 |
| 2.1897 | 84.2 | 3.0 | 2.7 | 10.1 | 79.2 | 18.1 | 1.5 | 1.2 |

TABLE 5-continued

Distribution of formic acid between water and benzyl formate at 20° C.

| HCCOH | Benzyl formate, % by wt. | | | | Water, % by wt. | | | |
|-------|---|---|---|---|---|---|---|---|
| g | E | HCOOH | H2O | BA | H2O | HCOOH | E | BA |
| 3.2370 | 79.9 | 4.7 | 3.3 | 12.1 | 73.4 | 23.3 | 1.8 | 1.5 |
| 4.3963 | 73.9 | 7.1 | 4.7 | 14.3 | 65.8 | 30.3 | 2.1 | 1.8 |

E Benzyl formate
BA Benzyl alcohol

We claim:
1. A process for the preparation of formic acid, comprising the following steps:
   a) hydrolysis of methyl formate to give a mixture of water, formic acid, methanol and excess methyl formate;
   b) removal of the methanol and excess methyl formate from form the mixture of water, formic acid, methanol and excess methyl formate by distillation to give aqueous formic acid;
   c) extraction of the aqueous formic acid with at least one formic acid ester selected from the group consisting of ethylene glycol diformate, diethylene glycol diformate, propane-1,2-diol diformate, propane-2,3-diol diformate, dipropylene glycol diformate, butane-2,3-diol diformate, butane-1,4-diol diformate, benzyl formate, cyclohexyl formate, 2-phenylformate, and 2-ethylhexylformate, to give a mixture of said at least one formic acid ester and formic acid under distillation conditions in an extractive distillation column;
   d) separation of said at least one formic acid ester and formic acid by distillation.
2. A process as claimed in claim 1, wherein the formic acid ester is benzyl formate.
3. A process as claimed in claim 1, where the formic acid ester is produced from its corresponding alcohol and formic acid in the extractive distillation column.
4. A process as claimed in claim 1, where the extractive distillation column is operated at ambient pressure.
5. A process as claimed in claim 1, where the formic acid ester is introduced at or close to the top of the extractive distillation column.
6. A process as claimed in claim 1, where a phase separator is provided at the top of the extractive distillation column.
7. A process as claimed in claim 1, where the mixture of formic acid ester and formic acid is separated under reduced pressure in a vacuum column.
8. A process as claimed in claim 1, where the formic acid ester is circulated between the extractive distillation column and the vacuum column.

* * * * *

UNITED STATES PATENT AND TRADEMARK OFFICE
CERTIFICATE OF CORRECTION

PATENT NO. : 6,713,649 B1
DATED : March 30, 2004
INVENTOR(S) : Hladiy et al

It is certified that error appears in the above-identified patent and that said Letters Patent is hereby corrected as shown below:

Title page,
Item [86], PCT No., "PCT/EP01/11046" should be -- PCT/EP00/11046 --.

Signed and Sealed this

Twenty-fifth Day of January, 2005

JON W. DUDAS
*Director of the United States Patent and Trademark Office*